United States Patent [19]

Finlayson et al.

[11] 4,164,215

[45] Aug. 14, 1979

[54] ELECTRODE SWITCHING MEANS FOR USE IN A DEFIBRILLATOR

[75] Inventors: Dana C. Finlayson, Natick; Ronald D. Gatzke; Robert L. Stettiner, both of Lexington, all of Mass.

[73] Assignee: Hewlett-Packard Company, Palo Alto, Calif.

[21] Appl. No.: 805,552

[22] Filed: Jun. 10, 1977

[51] Int. Cl.$^2$ .............................................. A61B 5/04
[52] U.S. Cl. ................................. 128/696; 128/419 D
[58] Field of Search ............ 128/2.06 B, 2.1 P, 419 D

[56] References Cited

U.S. PATENT DOCUMENTS

| | | | |
|---|---|---|---|
| 3,513,850 | 5/1970 | Weber | 128/419 D |
| 3,548,807 | 12/1970 | Crovella | 128/2.06 R |
| 3,587,562 | 6/1971 | Williams | 128/2.06 B |
| 3,611,174 | 10/1971 | Day | 128/2.06 B |
| 3,653,387 | 4/1972 | Ceier | 128/2.06 R |
| 3,690,313 | 9/1972 | Weppner et al. | 128/2.06 B |
| 3,757,778 | 9/1973 | Graham | 128/2.06 R |
| 3,994,286 | 11/1976 | Svensson | 128/2.06 B |

*Primary Examiner*—William E. Kamm
*Attorney, Agent, or Firm*—Donald N. Timbie

[57] ABSTRACT

A defibrillator is described having separate amplifiers for the paddles and the ECG electrodes and means for supplying cardiographic signals to an output amplifier from the amplifier associated with the ECG electrodes when they are properly attached to the patient and for automatically coupling cardiographic signals to the output amplifier from the amplifier associated with the paddles if any combination of the ECG electrodes become improperly attached.

8 Claims, 1 Drawing Figure

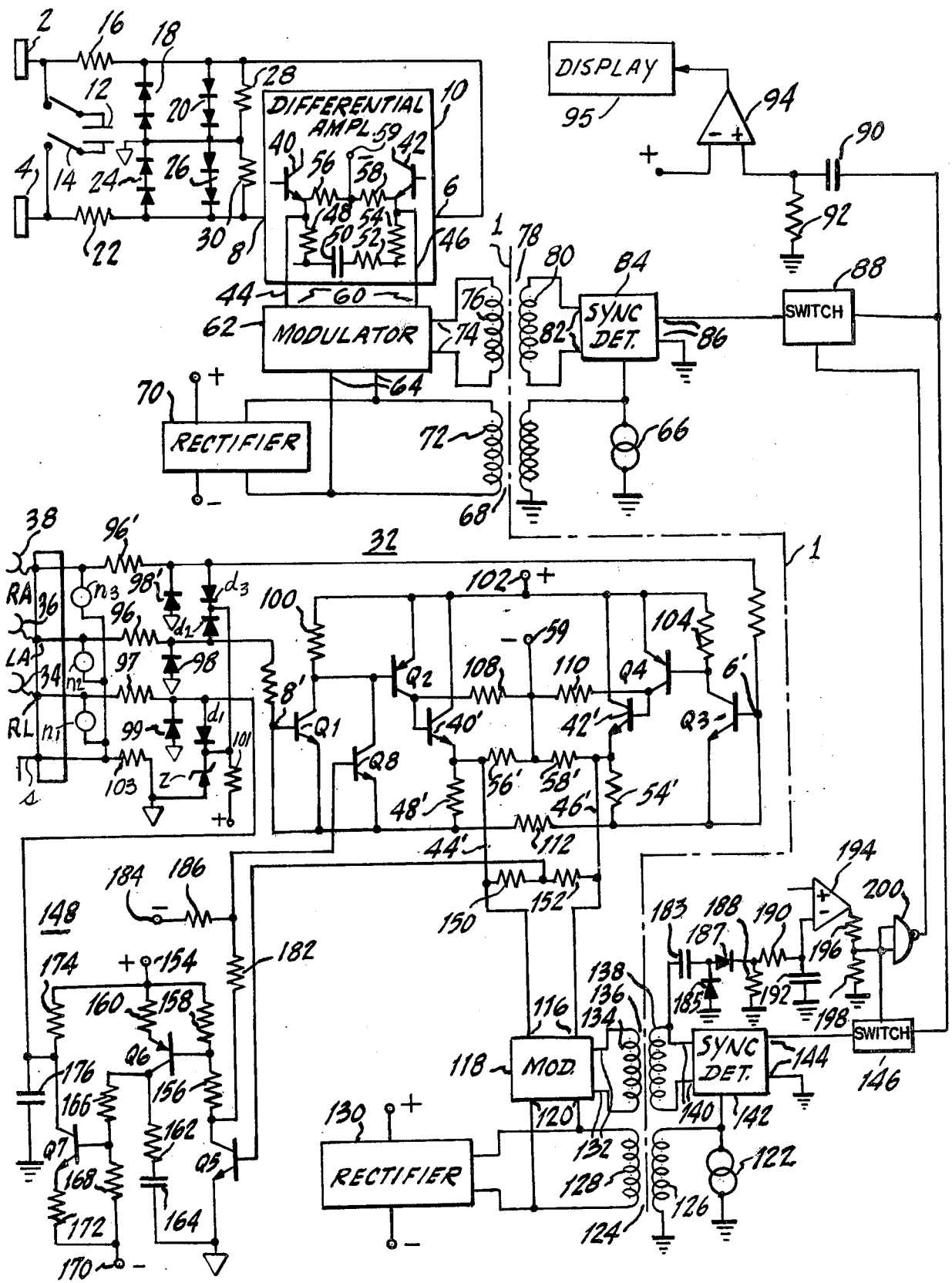

ELECTRODE SWITCHING MEANS FOR USE IN A DEFIBRILLATOR

BACKGROUND OF THE INVENTION

When a heart goes into fibrillation its muscles contract in a randomly related manner so that it cannot pump blood. In this condition the electrical charges that control the muscle action are improperly distributed, but if they are properly oriented, for even an instant of time, it is possible that the heart can resume normal operation. Reorientation may be accomplished by passing electrical current through the heart with an instrument known as a defibrillator. It operates by discharging current from a storage capacitor through paddle electrodes that are pressed against the body of a patient at certain locations relative to the heart.

During fibrillation, the timing of the pulse of defibrillation discharge current is unimportant, but once the heart acquires some degree of proper rhythm, an ill timed discharge can cause the heart to revert to a state of fibrillation and the patient may die. For this reason cardiographic signals are displayed on an oscilloscope. If the waveforms of heart action on the oscilloscope indicate a condition of fibrillation, the discharge can be initiated manually, but if they indicate a rhythmic condition, the discharge must be controlled automatically by synchronizing circuits so that it occurs at the correct point in the heart cycle. The signals for the oscilloscope, as well as for the synchronizing circuits, can be derived from the paddle electrodes, but signals of better quality can be derived from a set of ECG electrodes. The selection has been made by a manual switch and applied to an amplifier that is common to both the oscilloscope and the synchronizing circuits. The switch is expensive and bulky because it must withstand the discharge applied to the paddles, and the quality of the signals provided by the common amplifier is impaired by virtue of the fact that it must be designed so as to work with the paddles as well as with the ECG electrodes. Of greater importance, however, is the fact that if the switch is set to select signals from the ECG electrodes and one of them falls off or becomes maladjusted, as can easily occur under the circumstances in which a defibrillator is used, the signal falls at a time when it is vitally needed. If this is noticed, precious seconds are lost, but if it is not noticed, the consequent disappearance of the ECG waveform from the oscilloscope may be erroneously interpreted to mean that the patient has cardiac standstill, and efforts that might save his life may be misdirected, leading to death.

BRIEF DISCUSSION OF THE INVENTION

In accordance with this invention, two preamplifiers are provided, one for the ECG electrodes and one for the paddles. If the ECG electrodes are properly attached, the cardiographic signals are obtained from them, but if one or more of these electrodes become maladjusted, the signals are automatically obtained from the paddles. Thus, even in the confusion that normally exists when a defibrillator is in use, the better signal is automatically available. Other advantages that result from the arrangement include the fact that the ECG amplifier can be designed so as to produce more accurate waveforms and the fact that the bulk and expense of the switches used can be reduced because they do not have to withstand the electrical discharge voltage applied to the paddles.

DISCUSSION OF THE PREFERRED EMBODIMENT

Defibrillator paddles 2 and 4 are respectively coupled to the inputs 6 and 8 of a differential amplifier 10. In order to send a pulse of current through the heart, the paddles 2 and 4 are pressed against certain locations on the patient's chest and a storage capacitor 12 is discharged through them by connecting its opposite sides to the paddles via a switch 14. In order to protect the amplifier 10 from the high voltage pulse applied to the paddles, a voltage divider is connected between each paddle and the input of the amplifier 10 to which it is coupled. For the paddle 2 a resistor 16 is connected in series with a pair 18 of serially connected similarly poled diodes between the paddle 2 and the amplifier reference potential, commonly referred to as guard. To protect against voltages of the opposite polarity, another pair 20 of serially connected diodes having a polarity opposite to the pair 18 is connected in shunt therewith. For the paddle 4 a resistor 22 is connected in series with a pair 24 of serially connected similarly poled diodes between the paddle 4 and guard, and another pair 26 of serially connected diodes that are oppositely poled from the pair 24 are connected in shunt therewith. Resistors 28 and 30 that are connected in shunt with the pairs of diodes 20 and 26 provide bias for the input transistors of the amplifier 10, not shown, that are connected to the inputs 6 and 8.

The differential amplifier 10 may have many forms, but it is assumed that it will have the same general configuration as the differential amplifier 32 that will be discussed in detail in connection with the ECG electrodes 34, 36 and 38. Only the emitter follower output stages, including the transistors 40 and 42 are shown in the amplifier 10. A 6 db/octave roll off below a frequency of 0.7 Hz is provided at the output leads 44 and 46 that are respectively connected to the emitters of the transistors 40 and 42 by connecting a resistor 48, a capacitor 50, a resistor 52 and a resistor 54 in series between the emitters of the transistors 40 and 42. Emitter bias is provided by respectively connecting resistors 56 and 58 between the emitters and a point 59 of negative potential. The 6 db/octave roll off at the output leads 44 and 46 discriminates against the relatively high proportion of energy of the defibrillator recovery pulse that appears at the lower frequencies, and it also reduces the low frequency noise signals caused by motion of the paddles 2 and 4 on the body when they are being used to provide the cardiographic signals.

The push pull output between the leads 44 and 46 is applied to one input 60 of a modulator 62 so as to modulate the amplitude of the carrier waves supplied to another input 64 of the modulator 62 from a source 66 via a transformer 68. A rectifier 70 is coupled to the secondary winding 72 so as to provide suitable operating potentials for the circuits described.

Transference of the signals from the output 74 of the modulator 62 to the grounded circuits is achieved by coupling the output 74 to the primary winding 76 of a transformer 78. The voltage across the secondary winding 80 of the transformer 78 is applied to an input 82 of a synchronous detector 84. The other input of the synchronous detector 84 is supplied with carrier waves from the source 66 so as to recover amplified signals corresponding to the voltages existing between the paddles 2 and 4 and provide them at an output 86, one side of which is grounded. The ungrounded side of the output 86 is applied to one terminal of a normally open switch 88, and the other terminal of the switch is coupled via a capacitor 90 and a resistor 92 to the noninverting input of an amplifier 94. The capacitor 90 and the resistor 92 provide a 6 db/octave roll off for frequencies below 0.5 cycles. The output of the amplifier 94 is coupled to a display device 95.

The ECG electrodes 36, 38 and 34 are coupled as follows: Any increase in the potential of the body of the patient at the electrode 36 resulting from the discharge of the storage capacitor 12 through the paddles 2 and 4 is reduced by connecting a resistor 96 and a diode 98 in series between the jack LA and guard. Inasmuch as the electrocardiographic signals are much smaller than the minimum potential required to make the diode 98 conduct, their amplitude is not reduced, and they are coupled to one input 8' of the differential amplifier 32. The electrode 38 is coupled to the other input 6' of the amplifier 32 via the same kind of circuits just described in which corresponding components are indicated by the same numerals primed. A resistor 97 and a diode 99 connected in series between the right leg electrode 34 and guard reduce the voltage of a discharge pulse at their junction so as to protect the right leg drive circuit to be described that is connected thereto. Neon bulbs $n_1$, $n_2$, and $n_3$, are respectively connected between guard and the electrodes 34, 36 and 38 so as to protect the circuits coupled to them from high voltage that might occur during discharge. Further protection is provided by diodes $d_1$, $d_2$ and $d_3$, that are respectively connected between the ungrounded sides of the diodes 99, 98 and 98' and a resistor 101 that is connected to a point of +5 V. Still further protection is provided by a Zener diode Z that is connected between guard and the junction of the resistor 33 with the diodes $d_1$, $d_2$ and $d_3$. Shielding s is connected to guard by a resistor 103.

In the differential amplifier 32 components corresponding to those shown in the differential amplifier 10 are indicated by the same numerals primed. The base of an input transistor $Q_1$ is connected to the input 8' and its collector is connected to the base of a voltage amplifier $Q_2$ that has its collector in turn connected to the base of an emitter follower 40'. A resistor 100 is connected between a point 102 of positive potential and the collector of $Q_1$ and the base of $Q_2$ so as to provide biasing potentials therefore. The emitter of $Q_2$ and the collector of the emitter follower 40' are connected to the point 102. The other half of the amplifier 32 is the mirror image of that just described. The base of a second input transistor $Q_3$ is connected to the input terminal 6' and the collector of $Q_3$ is connected to the base of a voltage amplifier $Q_4$ that has its collector in turn connected to the base of an emitter follower 42'. A resistor 104 is connected between the positive point 102 and the collector of $Q_3$ and the base of $Q_4$ so as to provide biasing potentials therefore. The emitter of $Q_4$ and the collector of the emitter follower 42' are connected to the point 102 of positive potential. Negative bias is supplied from the point 59' to the collectors of $Q_2$ and $Q_4$ via resistors 108 and 110 and to the emitters of the emitter followers 40' and 42' via the resistors 56' and 58'. The emitters of $Q_1$ and $Q_3$ are connected to the resistors 48' and 54' and a resistor 112 is connected between the emitters of $Q_1$ and $Q_3$.

The output leads 44' and 46' of the amplifier 32 are connected to one input 116 of a modulator 118 so as to modulate the amplifier of carrier wave signals supplied to another input 120 from a source 122 via transformer 124 having a primary winding 126 and secondary winding 128. A rectifier 130 is coupled to the secondary winding 128 so as to provide positive and negative operating potentials for the floating circuits associated with the ECG electrodes 34, 36 and 38 such as, for example the potentials for the points 102 and 59.

The signals provided at the output 132 of the modulator 118 are coupled to the grounded world by coupling its output 132 to the primary winding 134 of a transformer 136. The secondary winding 138 is connected to the input 140 of a synchronous detector 142 wherein it is combined with the carrier waves supplied to another input from the source 122. The signals at the output 144 of the synchronous detector 142 are an amplified version of the signals existing between the ECG electrodes 36 and 38. They are applied to one side of a normally closed switch 146, and the other side of the switch is connected to the capacitor 90.

A right leg drive circuit 148 operates in a known manner to invert the average voltage between the output leads 44' and 46' and guard. The action of this circuit is to cause the reference potential, or guard, of the floating circuits to track the common mode potential that is produced on the patient by lights and other electrical sources. The circuit 148 is controlled by connecting the base of a transistor $Q_5$ to the junction of resistors 150 and 152 that are connected in series between the output leads 44' and 46' of the differential amplifier 32. Any variations in potential of the body due to electric lights, cables, etc. cause the potential of the ECG electrodes 36 and 38 to vary in like manner and produce a similar voltage variation at the junction of the resistors 150 and 152. The emitter of $Q_5$ is connected to guard and the collector to a point 154 of positive potential via series resistors 156 and 158. A resistor 160, the emitter-collector path of a transistor $Q_6$, a resistor 162 and a capacitor 164 are connected in series between the positive point 154 and guard in the order named, and the base of $Q_6$ is connected to the junction of the resistors 156 and 158. Resistors 166 and 168 are connected in series between the collector of $Q_6$ and a point 170 of negative potential. The junction of the resistors 166 and 168 is connected to the base of a transistor $Q_7$. A resistor 172 is connected between the point 170 of a negative potential and the emitter of $Q_7$, and a resistor 174 is connected between the collector of $Q_7$ and the point 154 of positive potential. The collector of $Q_7$ is bypassed to guard by a capacitor 176 and is connected to the junction of the resistor 97 and the diode 99 and via the resistor 97 to the jack RL to which the electrode 34 is connected.

Thus, the circuit 148, the right leg electrode 34, the body of the patient and the differential amplifier 32 are connected in a closed loop that operates to keep the floating ground, or guard, at 1.2 volts below the potential of the body. This potential is established by the voltage difference between the base and emitter of $Q_5$.

In accordance with the invention, the signals supplied to the output amplifier 94 are to be derived from ECG electrodes 36 and 38 if all three ECG electrodes are properly attached. If either of these electrodes 36 or 38 falls off or has too high a resistance between it and the body of the patient, the drive from the electrode 34 to the base of one of the input transistors $Q_1$ or $Q_3$ is interrupted so as to cause the output of the otherwise balanced amplifier 32 to become unbalanced. If the right leg electrode 34 falls off or has too high an impedance, a normally nonconducting transistor $Q_8$ that is connected in shunt with $Q_1$ is made to conduct so as to unbalance the differential amplifier 32. This is accomplished by connecting the base of the transistor $Q_8$ to the collector of $Q_5$ via a resistor 182 and to a point 184 of negative potential via a resistor 186. The values of the resistors 182 and 186 and the potentials at the collector of $Q_5$ and at the point 184 are such that when $Q_5$ is conducting, as when all electrodes are properly connected, the transistor $Q_8$ is cut off, but when the electrode 34 is improperly attached, the potential at the junction of the resistors 150 and 152 becomes negative cutting off $Q_5$ and causing its collector to become positive. This makes the base of $Q_8$ go positive so that $Q_8$ conducts. The same action takes place if both ECG electrodes 34 and 36 fall off.

When the amplifier 32 is unbalanced for any of the above reasons, a larger than normal voltage is produced between its output leads 44' and 46' so as to increase the amplitude of the modulation of the carrier wave at the secondary winding 138 of the transformer 136. One end of the secondary winding 138 is coupled via a capacitor 183 to the cathode of a rectifier 185 having its anode connected to ground and to the anode of a rectifier 187 having its cathode connected to ground via a resistor 188. A resistor 190 and a capacitor 192 are connected in series parallel relationship with the resistor 188. This circuit produces a positive D.C. voltage at the inverting input of a comparator 194 that is proportional to the amplitude of the modulation of the carrier wave appearing across the secondary winding 138. The resistor 190 and the capacitor 192 delay any change in this positive potential so as to prevent any inadvertent changes in operation during the momentary amplifier overloads experienced during a discharge of current between the paddles 2 and 4. When the differential amplifier 32 is balanced, the positive potential is less than the positive potential applied to the noninverting input of the comparator 194, but when it exceeds it, the output of the amplifier 194 appearing across its load resistors 196 and 198 becomes negative. Their junction is connected to the switch 146 and also to the input of an inverter 200. The output of the inverter 200 is connected to the switch 88. When the junction of the resistors 196 and 198 is positive, the switch 146 is turned on and the switch 88 is turned off so that the output amplifier 94 is supplied with signals from the ECG electrodes 36 and 38, but when the junction of the resistors 196 and 198 is negative, the switch 146 is opened and the switch 88 is closed so that the output amplifier 94 is supplied with signals from the paddles 2 and 4.

Thus, whether or not the ECG electrodes 34, 36 and 38 are properly attached, signals representing heart action are provided to the amplifier 94, but if the ECG electrodes are properly attached, the better signals they provide will automatically be applied to the amplifier 94.

No attempt is made to describe all of the variations that may be made within the scope of this invention but a few are as follows: Instead of modulating the amplitude of a carrier wave with the cardiographic waveforms derived from the paddles 2 and 4 or from the ECG electrodes 36 and 38 and coupling them by transformers to the grounded world, the cardiographic signals could be used to modulate the intensity of a beam of light which is directed to a photoelectric device. Whereas imbalance in the balanced amplifier 32 is a highly satisfactory means for detecting a significant change in the impedance between an ECG electrode and the body of a patient, other means responsive to such change in impedance could be used. For example, high frequency waves could be applied to the right leg electrode 34 and detected at the electrodes 36 and 38. Failure of the detected signal would indicate that one of the leads is maladjusted, and the failure could be used to operate the switches so as to use the cardiographic signals provided by the paddle electrodes 2 and 4.

What is claimed is:

1. Apparatus for use in a defibrillator comprising the combination of an output for coupling to a monitor, a first pair of inputs adapted for connection to a pair of paddle electrodes, means including a first switch for coupling the signals appearing between said first pair of inputs to said output, said switch being normally open, a second pair of inputs adapted for connection to a pair of ECG electrodes, means including a second switch for coupling signals appearing between said second pair of inputs to said output, said switch being normally closed, and means responsive to a given change in the impedance at said second pair of inputs for opening said second switch and closing said first switch.

2. A circuit for use in a defibrillator comprising the combination of an output for coupling to a monitor, a first pair of inputs adapted for connection to a pair of paddle electrodes, means including a first switch for coupling the signals appearing between said first pair of inputs to said output, said switch being normally open, a second pair of inputs adapted for connection to a pair of ECG electrodes, a differential amplifier having a first input coupled to one of said second pair of inputs, a second input coupled to the other of said second pair of inputs, and an output, a normally closed second switch connected between the output of said differential amplifier and said output, and means responsive to a predetermined change in the signal at the output of said differential amplifier occurring when the signal applied to one of said second pair of inputs decreases below a predetermined level to open said second switch and close said first switch 3. A circuit as set forth in claim 2 having an input adapted to be connected to a third ECG electrode, means responsive to the average voltage across the output of said differential amplifier for tending to maintain said third ECG electrode at a predetermined direct current voltage, and means responsive to a predetermined change in the average potential across the output of said differential amplifier for unbalancing said differential amplifier.

4. Apparatus for use in a defibrillator comprising the combination of, a pair of paddle electrodes, a first amplifier having an input and an output, means for coupling said input to said paddle electrodes, an output amplifier having an input and an output for coupling to a monitor, means including a normally open switch coupling the output of said first amplifier to the input of said output amplifier, first, second and third ECG electrodes, a differential amplifier having two inputs and an output, means coupling said first ECG electrode to one of said (input stages) inputs of said differential amplifier so that (bias currents) drive therefor may be derived via said first ECG electrode, means coupling said second ECG electrode to the other of said (input stages) inputs of said differential amplifier so that (bias currents) drive therefor may be derived via said second ECG electrode, means including a normally closed switch for coupling the output of said differential amplifier to said input of said output amplifier, means responsive to the average voltage across the output of said differential amplifier for maintaining said third ECG electrode at a predetermined value of direct current voltage, whereby said third ECG electrode provides bias currents to said first and second ECG electrodes when all of said ECG electrodes are in proper electrical contact with the body of a patient, and whereby said differential amplifier is unbalanced if either of said first or second ECG electrodes does not make proper electrical contact with the body, means responsive to a predetermined change in said average voltage at the output of said differential amplifier for unbalancing said differential amplifier, and means responsive to an imbalance in said differential amplifier for opening said normally closed switch and closing said normally open switch.

5. A circuit for use in a defibrillator comprising:

a first input to which a first paddle electrode may be connected and a second input to which a second paddle electrode may be connected, a first transformer having primary and secondary windings, means coupled between said first and second inputs and said primary winding of said first transformer for producing a voltage across said primary winding that is proportional to any difference in potential between said first and second inputs, third and fourth inputs to which first and second ECG electrodes may be connected, a second transformer having primary and secondary windings, a differential amplifier having two inputs and a differential output, means coupling said third input to one of said amplifier inputs and means coupling said fourth input to the other amplifier input, means coupling said differential output of said differential amplifier across said primary winding of said second transformer, an output amplifier having an input and an output, means including a normally open switch connected between said secondary winding of said first transformer to said input of said output amplifier, means including a normally closed switch connected between said secondary winding of said second transformer and said input of said output amplifier, and means responsive to a voltage across said secondary winding of said second transformer that is in excess of a predetermined value to close said normally open switch and open said normally closed switch.

6. A circuit as set forth in claim 5 a fifth input to which a third electrode may be connected, means responsive to the average voltage of the output of said differential amplifier for maintaining said third electrode at a predetermined potential, and means responsive to a predetermined value of the average voltage for unbalancing said differential amplifier.

7. A circuit for use in a defibrillator comprising the combination of a first differential amplifier having two inputs and differential output, impedance means coupled to said output for reducing the output voltage as its frequency drops below a given value, a first transformer having primary and secondary windings, means for applying a carrier wave to said primary winding, a modulator having two inputs and an output, means coupling one of said inputs of said modulator to said differential output of said differential amplifier, means coupling the other of said inputs of said modulator to said secondary winding of said first transformer, a second transformer having primary and secondary windings, means coupling said primary winding of said second transformer to said output of said modulator, a synchronous detector having two inputs and an output, means coupling one of said inputs of said synchronous detector to said secondary winding of said second transformer, means coupling the other input of said synchronous detector to said means for providing a carrier wave, an output amplifier having an input and an output, a normally open switch having one side connected to the output of said synchronous demodulator, a filter coupled between the other side of said switch and said input of said output amplifier, said filter having a response that decreases with frequency below a predetermined value, a second differential amplifier having two inputs and a differential output, a third transformer having primary and secondary windings, means for applying a carrier wave to said primary winding for said third transformer, a second modulator having two inputs and an output, means coupling one of said inputs of said second modulator to said differential output of said second differential amplifier, means coupling the other of said inputs of said second modulator to said secondary winding of said third transformer, a fourth transformer having primary and secondary windings, means coupling said primary winding of said fourth transformer to the output of said second modulator, a second synchronous detector having two inputs and an output, means coupling one of said inputs of said second synchronous detector to said secondary winding of said fourth transformer, means coupling the other of said inputs of said second synchronous detector to said means for applying a carrier wave to said primary winding for said third transformer, a normally closed switch coupled between said output of said second synchronous detector and said filter, and means coupled to the secondary winding of said fourth transformer for closing said normally open switch and opening said normally closed switch when the voltage across a winding of said fourth transformer exceeds a predetermined value.

8. A circuit as set forth in claim 7 means coupled to said differential output for said second differential amplifier to provide a voltage equal to the average voltage thereof, a right leg drive circuit coupled to said latter means, and means responsive to the average voltage provided by said last named means and coupled to one side of said second differential amplifier for unbalancing said amplifier when said average voltage acquires a predetermined value.

* * * * *

UNITED STATES PATENT AND TRADEMARK OFFICE
CERTIFICATE OF CORRECTION

PATENT NO. : 4,164,215
DATED : August 14, 1979
INVENTOR(S) : Dana C. Finlayson et al It is certified that error appears in the above-identified patent and that said Letters Patent are hereby corrected as shown below:

| Column 2 | line 10 | "di" should read -- dis -- |
| Column 7 | line 8 | delete "(input stages)" |
| | line 9 | delete "(bias currents)" |
| | line 12 | delete "(input stages)" |
| | line 13 | delete "(bias currents)" |

Signed and Sealed this

Fourth Day of December 1979

[SEAL]

Attest:

SIDNEY A. DIAMOND

Attesting Officer

Commissioner of Patents and Trademarks